(12) United States Patent
Borrello

(10) Patent No.: US 6,557,553 B1
(45) Date of Patent: May 6, 2003

(54) ADAPTIVE INVERSE CONTROL OF PRESSURE BASED VENTILATION

(75) Inventor: Michael Borrello, Carlsbad, CA (US)

(73) Assignee: Mallinckrodt, Inc., Hazelwood, MO (US)

( * ) Notice: Subject to any disclaimer, the term of this patent is extended or adjusted under 35 U.S.C. 154(b) by 223 days.

(21) Appl. No.: 09/655,969

(22) Filed: Sep. 5, 2000

(51) Int. Cl.⁷ .................... A61M 16/00; A62B 7/00
(52) U.S. Cl. ................... 128/204.18; 128/204.21; 600/529; 600/533; 600/538
(58) Field of Search ............ 128/204.18, 204.21, 128/204.23, 204.22; 600/529, 533, 538

(56) References Cited

U.S. PATENT DOCUMENTS

| | | | |
|---|---|---|---|
| 3,713,436 A | * 1/1973 | Hardway, Jr. ............... 600/529 |
| 3,857,385 A | * 12/1974 | Hampl ....................... 600/529 |
| 3,871,371 A | * 3/1975 | Weigl ...................... 128/204.18 |
| 3,923,056 A | * 12/1975 | Bingmann et al. ...... 128/204.23 |
| 4,031,885 A | * 6/1977 | Davis et al. ............... 600/533 |
| 4,036,221 A | * 7/1977 | Hillsman et al. ....... 128/204.18 |
| 4,036,222 A | * 7/1977 | Gillard et al. ............. 600/529 |
| 4,051,843 A | * 10/1977 | Franetzki et al. .......... 600/529 |
| 4,082,088 A | * 4/1978 | Franetzki et al. .......... 600/529 |
| 4,197,859 A | * 4/1980 | Prestele ..................... 600/529 |
| 4,220,161 A | * 9/1980 | Berlin et al. ............... 600/529 |
| 4,259,967 A | * 4/1981 | Vooren et al. .............. 600/529 |
| 4,336,590 A | * 6/1982 | Jacq et al. ................... 364/418 |
| 4,351,344 A | * 9/1982 | Stenzler ..................... 600/529 |
| 4,444,201 A | * 4/1984 | Itoh ............................ 600/529 |
| 4,671,297 A | * 6/1987 | Schulze, Jr. ................ 600/529 |
| 4,802,492 A | * 2/1989 | Grunstein ................... 600/529 |
| 4,889,116 A | 12/1989 | Taube | |
| 4,972,842 A | * 11/1990 | Korten et al. ............... 600/529 |
| 4,986,268 A | 1/1991 | Tehrani | |
| 5,233,998 A | * 8/1993 | Chowienczyk et al. ...... 600/529 |
| 5,261,397 A | * 11/1993 | Grunstein ................. 128/204.18 |
| 5,271,389 A | 12/1993 | Isaza et al. | |
| 5,303,698 A | 4/1994 | Tobia et al. | |
| 5,315,989 A | 5/1994 | Tobia et al. | |
| 5,316,009 A | * 5/1994 | Yamada ...................... 600/529 |
| 5,316,010 A | * 5/1994 | Brown ....................... 600/529 |
| 5,319,540 A | 6/1994 | Isaza et al. | |
| 5,365,922 A | 11/1994 | Raemer | |
| 5,388,575 A | 2/1995 | Taube | |
| 5,429,123 A | 7/1995 | Shaffer et al. | |
| 5,517,983 A | * 5/1996 | Deighan et al. ....... 128/204.23 |
| 5,660,170 A | 8/1997 | Rajan et al. | |
| 5,682,877 A | 11/1997 | Mondry | |
| 5,692,497 A | 12/1997 | Schnitzer et al. | |
| 5,715,812 A | * 2/1998 | Deighan et al. ....... 128/204.23 |
| 5,735,267 A | 4/1998 | Tobia | |
| 5,743,253 A | 4/1998 | Castor et al. | |
| 5,752,509 A | 5/1998 | Lachmann et al. | |
| 5,865,168 A | 2/1999 | Isaza | |
| 5,876,352 A | * 3/1999 | Weismann ................... 600/529 |
| 6,068,602 A | * 5/2000 | Tham et al. ................ 600/533 |
| 6,142,150 A | * 11/2000 | O'Mahoney ........... 128/205.18 |
| 6,257,234 B1 | * 7/2001 | Sun ......................... 128/204.18 |
| 6,332,463 B1 | * 12/2001 | Farrugia et al. ....... 128/204.18 |

OTHER PUBLICATIONS

Tobin et al., Principles & Practice of Mechanical Ventilation, 1994 pp. 56–58.*

\* cited by examiner

*Primary Examiner*—Aaron J. Lewis
*Assistant Examiner*—Joseph F. Weiss, Jr.
(74) *Attorney, Agent, or Firm*—Fulwider Patton Lee & Utecht, LLP

(57) ABSTRACT

The adaptive control method for controlling pressure based ventilation utilizes a specific regulator structure designed according to a linear model of the patient/ventilator system. The same model is also used to derive a real time estimate of patient airway resistance, lung compliance, and the connecting tube compliance. These estimates are used to adjust regulator parameters in real time such that closed loop dynamics quickly approach those of a specified system. In the patient/connecting circuit system, G(s) inlet flow and circuit pressure are fed to a parameter estimator, and the output of the parameter estimator is used to adjust the parameters of the compensator, C(s).

10 Claims, 2 Drawing Sheets

ADAPTIVE INVERSE CONTROL OF PRESSURE BASED VENTILATION

BACKGROUND OF THE INVENTION

1. Field of the Invention

This invention relates generally to medical ventilators and control systems for medical ventilators, and more particularly concerns a system and method for adaptive inverse control of pressure based ventilation.

2. Description of Related Art

A patient receiving breath pressure support from a ventilator system typically receives breathing gas through a patient circuit of the ventilator. The patient circuit generally consists of two flexible conduits connected to a fitting called a patient wye. The free ends of the conduits are attached to the ventilator so that one conduit receives breathing gas from the ventilator's pneumatic system, and the other conduit returns gas exhaled by the patient to the ventilator. The volume of the exhaled gas may then be measured in a spirometer before it finally exits through an exhalation valve. The wye fitting is typically connected to the patient's breathing attachment or enclosure, which conducts breathing gas into the lungs, and conducts exhaled gas from the lungs to the exhalation branch of the patient circuit. The pneumatic system at the inspiratory end of the patient circuit is typically closed before a breath, and the exhalation valve at the exhalation end of the patient circuit is typically preceded by a one-way valve, to prevent gas from flowing retrograde in the exhalation branch of the patient circuit.

In pressure based ventilation, occurrences of low pressures in the exhalation limb of the patient's breathing gas circuit during the exhalation phase of the pressure supported breath can be a cause of concern for the patient unless they are carefully controlled. Pressures in the patient lung that fall below PEEP (Positive End Expiratory Pressure, a baseline pressure value) can impair a patient's lung function, and it can be important to maintain PEEP in a patient's lung to prevent collapse of the lung.

On the other hand, another current problem encountered in pressure based ventilation (PBV) is the control of overshoot of patient airway pressure during the inspiration cycle for pressure controlled type of ventilation. When the breath cycle is primarily controlled by the standard pressure and flow controllers, the patient can experience an overshoot in the airway pressure as a controller commands the flow valve opening to rapidly supply breathing gas to the patient during the initial phases of the inspiration. Thus, it is highly desirable to provide more accurate control of patient airway pressure during pressure based ventilation, since pressures that are too high or too low can have a number of undesirable effects.

Various types of adaptive controllers are known that have been used for controlling the functions of a patient ventilator. One type of adaptive control system for a medical ventilator for controlling flow and pressure based on the dynamic state of the ventilator utilizes a waveform generator that provides a desired pressure waveform. The flow control system has a switching logic block which can adaptively select either a flow delivery control algorithm or a flow exhaust control algorithm, based on the ratio of the pressure to the flow of gas. Both the delivery and exhaust control systems comprise feedback loops for minimizing the error between a target pressure signal from the waveform generator and a feedback signal corresponding to actual airway pressure.

In another type of adaptive controller for automatic ventilators, a pulse oximeter is used to optically determine hemoglobin saturation of the patient's blood, and the information is used to regulate the length of inspiration time, PEEP, and the fraction of inspired oxygen ($FiO_2$) supplied to a patient's breathing tube.

Another type of adaptive controller utilizes a feedback control loop having a transfer characteristic that is adaptive to the changing requirements of the patient so as to maintain the proper fractional amount of oxygen inspired. A closed loop non-invasive oxygen saturation control system is provided that utilizes an oximeter, and an algorithm that provides an adaptive filtering of the oxygen values for feedback control.

One known adaptive feedback control for a medical ventilator analyzes in the frequency domain the Laplace transfer functions that are determined for the elements of the ventilator system. To accurately control the mouth pressure, adaptive feedback control is used so that the control's lag term cancels the patient's lead term effect on the system. To precisely control the back pressure applied to a diaphragm valve, an expiratory pneumatic circle and control loop use a second closed loop controller. A control valve is operated based upon a pressure error signal generated by the controller. The inspiratory control function uses a control function algorithm, synchronization algorithm, time constant algorithm, and a resistance/compliance algorithm.

One of the most enduring and difficult problems in pressure based ventilation has been achieving pressure tracking performance across a wide range of patient conditions and ventilator settings. Non-stationary patient parameters, ventilator settings, and a wide selection of connecting circuit types can cause system dynamics to vary by several orders of magnitude. Classical control methods which use fixed gain controllers are typically unable to maintain consistent performance as these parameters vary. The designer must often resort to ad hoc modifications which, while marginally improving robustness, will likely require tradeoffs between overshoot of the trajectory, rise time, steady state accuracy, and stability margin. There thus remains a need for improving the control of pressure based ventilation.

The present invention meets these and other needs.

SUMMARY OF THE INVENTION

Briefly, and in general terms, the present invention provides for an adaptive control method which solves the pressure based ventilation control problem. This method utilizes a specific regulator structure designed according to a linear model of the patient/ventilator system. The same model is also used to derive a real time estimate of patient airway resistance, lung compliance, and the connecting tube compliance. These estimates are used to adjust regulator parameters in real time such that closed loop dynamics quickly approach those of a specified system. In the patient/connecting circuit system, inlet flow and circuit pressure are utilized for estimation of parameters for adjusting the pressure of gas to the desired pressure. The present invention provides for a unique gas pressure compensation, and a unique parameter estimation for providing parameters for compensation of the pressure of gas to the desired pressure, to provide for improved pressure based ventilator control. The present invention is able to provide consistent performance in pressure tracking over the entire range of patient conditions from small infant to large adult without having to balance the tradeoffs mentioned above. As a side benefit, the invention also provides patient and connecting circuit parameter measurements which can be used at a higher level in the ventilator control and can be used to possibly eliminate any need to run a system self test (SST) to determine these parameters.

While the method and apparatus of the present invention is described in the context of control of the inhalation cycle of a pressure based ventilation system, the method may also be applied to the exhalation cycle of both pressure based and volume controlled ventilation strategies. By modeling the exhalation aspects of the patient ventilator system using the methods of the invention, regulator parameters may be adjusted to quickly obtain a desired exhalation trajectory.

These and other aspects and advantages of the invention will become apparent from the following detailed description and the accompanying drawings, which illustrate by way of example the features of the invention.

DETAILED DESCRIPTION OF THE PREFERRED EMBODIMENTS

In pressure based ventilation, occurrences of low pressures in the exhalation limb of the patient's breathing gas circuit during the exhalation phase of the pressure supported breath can be a cause of concern for the patient unless they are carefully controlled. Pressures in the patient lung that fall below PEEP can impair a patient's lung function, and it can be important to maintain PEEP in a patient's lung to prevent collapse of the lung. When the breath cycle is primarily controlled by the standard pressure and flow controllers, the patient can also experience an overshoot in the airway pressure as a controller commands the flow valve opening to rapidly supply breathing gas to the patient during the initial phases of the inspiration. Thus, it is highly desirable to provide more accurate control of patient airway pressure during pressure based ventilation, since pressures that are too high or too low can have a number of undesirable effects. While various strategies have been used for pressure tracking performance across a wide range of patient conditions and ventilator settings, non-stationary patient parameters, ventilator settings, and a wide selection of connecting circuit types can cause system dynamics to vary by several orders of magnitude, making consistent performance of ventilators utilizing fixed gain controllers difficult to achieve.

Figure 3:
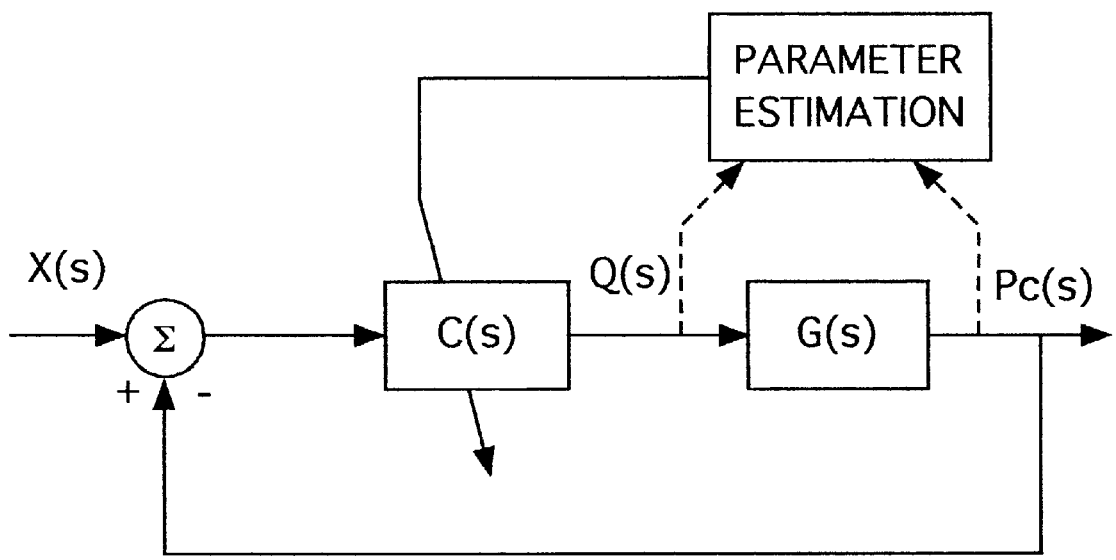
FIG. 3 is a schematic diagram of an adaptive pressure feedback control system according to the present invention.

As is illustrated in the drawings, the invention is embodied in an adaptive control method which solves the pressure based ventilation control problem. This method is based on a pure analytical approach, and uses a specific regulator structure designed according to a linear model of the patient/ventilator system. The same model is also used to derive a real time estimate of patient airway resistance, lung compliance, and the connecting tube compliance. These estimates are used to adjust regulator parameters in real time such that closed loop dynamics quickly approach those of a specified system. As is illustrated in FIG. 3, in the present invention, the patient/connecting circuit system, G(s) inlet flow and circuit pressure are fed to a parameter estimator. The output of the parameter estimator is used to adjust the parameters of the compensator, C(s).

In a first presently preferred aspect of the method of the invention, an algorithm is used to provide real time estimates of connecting circuit compliance, lung compliance and airway resistance using the standard recursive least squares method with forgetting factor. The algorithm has been implemented and tested in a Puritan Bennett 840 ventilator testbed using VisSim vector and matrix block operations.

Throughout this description, the terminology presented in Table 1 is used:

TABLE 1

Lung Model Symbols

| Symbol | Definition | Units |
| --- | --- | --- |
| $P_C$ | Pressure within the connecting circuit. Assumed to be measured at the patient wye or at the exhalation leg | cm $H_2O$ |
| $P_L$ | Lung Pressure, assumed to be measured at the distal end of the ETT tube | cm $H_2O$ |
| Q or $Q_V$ | Flow delivered into the connecting circuit | liters/sec |
| $C_T$ | Connecting circuit compliance | liters/cm $H_2O$ |
| $C_L$ | Compliance of the Lung | liters/cm $H_2O$ |
| R | Airway resistance | cm $H_2O$/liter/sec |
| C(s) | Compensator Transfer Function | liters/sec/cm/$H_2O$ |
| G(s) | Lung/Connecting Circuit Transfer Function | cm/$H_2O$/liters/sec |
| X(s) | Pressure trajectory | cm $H_2O$ |

Figure 1:
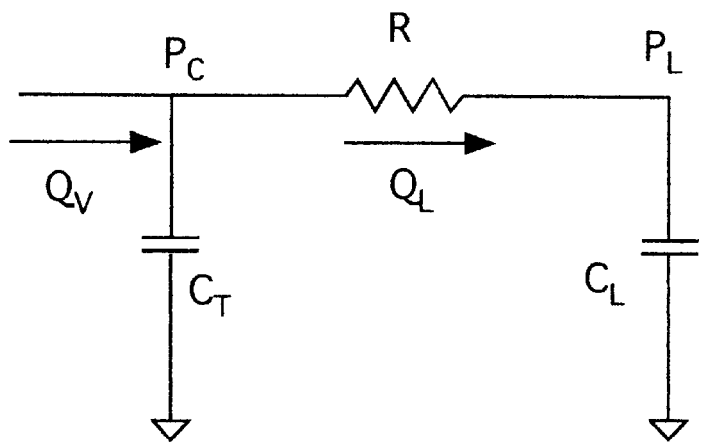
FIG. 1 is a schematic circuit diagram of a prior art lung/circuit system.

The RCC (R, airway resistance, $C_L$, compliance of the lung, and $C_T$, connecting circuit compliance) model illustrated in the circuit diagram presented in FIG. 1 was chosen to represent the lung/circuit system because of its relative simplicity, and ability to closely model ventilator pressure response. It removes the task of having to separately estimate the connecting circuit compliance for determining lung flow for resistance and compliance estimates by including the parameter as part of the least squares model. The RCC model of FIG. 1 can be expressed as a transfer function of circuit pressure to flow as:

$$\frac{Pc(s)}{Qv(s)} = \frac{\frac{1}{C_T}\left(s + \frac{1}{RC_L}\right)}{s\left(s + \frac{C_L + C_T}{RC_L C_T}\right)} \quad \text{(Eq. 1)}$$

Cross multiplication of the factors in Eq. 1 and division of all terms on each side of the equation by $(s+\lambda)^2$ results in an equation which can be split into separate parameter and measurement vectors serving as a parameter regression model of the form:

$$w(s) = \Theta^T \Phi(s) \quad \text{(Eq. 2)}$$

where $$\Theta^T = [\theta_1 \quad \theta_2 \quad \theta_3] \quad \text{(Eq. 3)}$$

$$\theta_1 = RC_L C_T \quad \text{(Eq. 4)}$$

$$\theta_2 = C_L + C_T \quad \text{(Eq. 5)}$$

$$\theta_3 = RC_L \quad \text{(Eq. 6)}$$

is the vector of parameters, and $$\Phi^T(s) = \left[ \frac{s^2}{(s+\lambda)^2} P_C(s) \frac{s}{(s+\lambda)^2} P_C(s) \frac{s}{(s+\lambda)^2} Qv(s) \right] \quad \text{(Eq. 7)}$$

is the vector of filtered input measurements and $$w(s) = \frac{1}{(s+\lambda)^2} Qv(s) \quad \text{(Eq. 8)}$$

is the filtered output measurement.

Filtering of each input and output measurement can be achieved by using cascade combinations of $1^{st}$ order low pass and high pass filters as follows:

$$\frac{1}{(s+\lambda)^2} = H_2(s)H_2(s) \quad \text{(Eq. 9)}$$

$$\frac{s}{(s+\lambda)^2} = H_1(s)H_2(s) \quad \text{(Eq. 10)}$$

$$\frac{s^2}{(s+\lambda)^2} = H_1(s)H_1(s) \quad \text{(Eq. 11)}$$

where $$H_1(s) = \frac{y(s)}{x(s)} = \frac{s}{s+\lambda} \quad \text{(Eq. 12)}$$

and $$H_2(s) = \frac{y(s)}{x(s)} = \frac{1}{s+\lambda} \quad \text{(Eq. 13)}$$

Both of these filters can be transformed to discrete time recursive approximations by assuming a sample time, T, and substituting the LaPlace operator, s, with equation 14 below. This expression uses the delay operator, $z^{-1}$ and accomplishes backward rectangular integration. The transformation maps s completely within the unit circle in the z plane, thus assuring stability.

$$s \rightarrow \frac{1-z^{-1}}{T} \quad \text{(Eq. 14)}$$

for $H_1(s)$ $$y(n) = \frac{1}{1+\lambda T}[x(n) - x(n-1) + y(n-1)] \quad \text{(Eq. 15)}$$

$$x(0) = y(0) = 0$$

and for $H_2(s)$ $$y(n) = \frac{1}{1+\lambda T}[Tx(n) + y(n-1)] \quad \text{(Eq. 16)}$$

$$y(0) = 0$$

The regression model can now be applied directly in a least squares formulation to solve for estimates of $\theta$ which can then be used to algebraically solve for the estimates of R, $C_L$ and $C_T$.

The working equations become:

Parameter estimate vector update equation $$\hat{\Theta}(n) = \hat{\Theta}(n-1) + K(n)[w(n) - \hat{\Theta}^T(n-1)\Phi(n)] \quad \text{(Eq. 17)}$$

Covariance matrix update equation $$\Gamma(n) = \frac{1}{\alpha}\left[\Gamma(n-1) - \left[\frac{\Gamma(n-1)\Phi(n)\Phi^T(n)\Gamma(n-1)}{\Phi^T(n)\Gamma(n-1)\Phi(n) + \alpha}\right]\right] \quad \text{(Eq. 18)}$$

Gain vector update equation $$K(n) = \frac{\Gamma(n-1)\Phi(n)}{\Phi^T(n)\Gamma(n-1)\Phi(n) + \alpha} \quad \text{(Eq. 19)}$$

where $\alpha<1$ is the forgetting factor. The closer $\alpha$ is to 1, the less responsive the estimator will be to parameter variations. The smaller $\alpha$ is, the more jumpy and uncertain the estimates will be. The asymptotic sample length (ASL) is defined as $$ASL \equiv \frac{1}{1-\alpha} \quad \text{(Eq. 20)}$$

The ASL provides a measure of the number of samples contributing to the estimate of $\Theta$. For estimates of respiratory mechanics at T=0.001sec, $\alpha=0.9997$ seems to provide a responsive yet stable estimate suitable for application in adaptive control of pressure based ventilation. For this value of $\alpha$ and T, 3.3 seconds of past measurement data contribute to the current estimate.

$\Gamma(n)$ is a 3×3, symmetric, positive definite matrix.

K(n) is a 3×1 vector, sometimes referred to as the Kalman gain.

The "^" written over $\Theta$ differentiates this symbol as an estimate of the vector symbol used to formulate the model.

To implement the equations, one must assume initial values for the parameter estimate vector elements and initial values for the covariance matrix elements. Arbitrary values can initially be assigned for the elements in the parameter estimate vector, after which the steady state estimate can be inspected. The steady state values can then be substituted as initial values to help reduce the size of start up transients in the estimation. The initial value of the covariance matrix should be chosen as a diagonal matrix. All diagonal elements can be equal to one another, but should be very large. For the respiratory mechanics estimator, the diagonal elements are equal to 1 e12. Off diagonal elements are all zero. The following steps for computation are recommended after defining initial values:

1. Capture the first measurements of flow and pressure, create φ, and calculate the gain vector.
2. Calculate the parameter estimate vector.
3. Calculate the covariance matrix
4. Update the parameter vector, measurement vector and covariance matrix for the next iteration
5. Repeat steps 1 through 4 at rate T.

Selection of $\lambda$ should be appropriate to filter any higher frequency, unmodeled dynamics from the assumed parametric model. Experience shows a pole at 10 Hz to handle the separation well. The elements of the parameter vector are actually linear combinations of the physical parameter estimates which must be solved from equations 4, 5 and 6. Some rearrangement results in the following:

$$\hat{C}_T = \frac{\hat{\theta}_1}{\hat{\theta}_3} \quad \text{(Eq. 21)}$$

$$\hat{C}_L = \hat{\theta}_2 - \frac{\hat{\theta}_1}{\hat{\theta}_3} \quad \text{(Eq. 22)}$$

$$\hat{R} = \frac{\hat{\theta}_1 \hat{\theta}_3^2}{\hat{\theta}_1 \hat{\theta}_2 \hat{\theta}_3 - \hat{\theta}_1^2} \quad \text{(Eq. 23)}$$

The estimator was implemented in the visual simulation language, VisSim, with an interface to pressure and flow sensors through real time data acquisition. VisSim provides real time graphical output so that the estimate could be tracked over time. VisSim was also used to provide volume control ventilation to persistently excite the dynamics. However, the algorithm could also be implemented in any similar suitable software language that can express these mathematical terms. Various combinations of lung resistance, circuit tubing compliance and lung compliance were run on the estimator. In the VisSim implementation, the parameter vector estimate was used to calculate an estimated (modeled) circuit pressure using equation 8. The estimator showed very rapid convergence of the estimates of R, $C_T$ and $C_L$ in under 100 msec with the modeled circuit pressure tracking almost immediately. Residuals measured on the order of 0.005 cm $H_2O$ at steady state. Estimates of R, $C_T$ and $C_L$ are time varying. This time variation is expected considering the real parameters are non-linear with flow, temperature and volume. On an average, the estimates do reflect values in the range of the known static values of these parameters. The variations about these averages are minimal which indicates that the assumed structure for the model was well chosen, but not absolutely precise. Other elements which were neglected in the model such as inertance could also account for these minor variations in time. If one is willing to accept the model structure, and the idea of time variation of parameters, then this estimator is well suited for determining R, $C_T$ and $C_L$. Whereas the estimator may not be entirely suitable for reporting equivalent static parameters of R, $C_T$ and $C_L$, it is highly suitable for application to adaptive control techniques.

Figure 2:
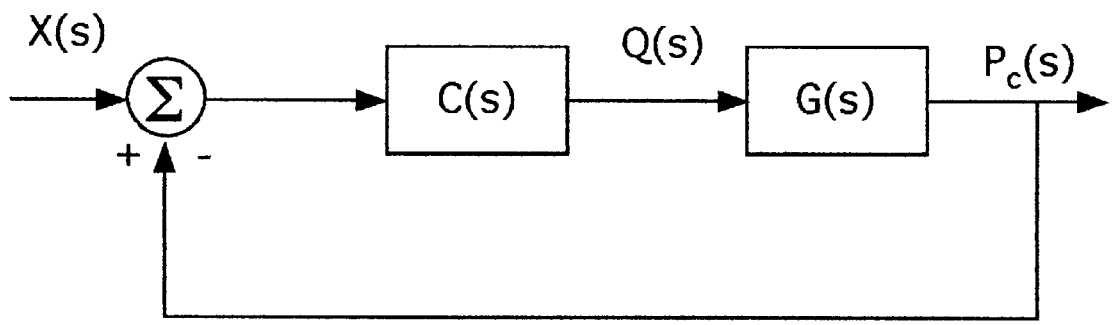
FIG. 2 is a schematic diagram of a prior art pressure feedback control system.

Pressure Tracking System:

Assume a pressure control feedback as shown in FIG. 2. G(s) represents the lung/circuit system as modeled by equation 1. C(s) represents a compensator to be designed such that the desired closed loop system, T(s) is achieved. The closed loop system can be described by the following transfer function:

$$T(s) = \frac{Pc(s)}{X(s)} = \frac{C(s)G(s)}{1 + C(s)G(s)} \quad \text{(Eq. 24)}$$

Solving for the compensator, C(s), necessary to get T(s) results in:

$$C(s) = \frac{T(s)}{G(s)(1 - T(s))} \quad \text{(Eq. 25)}$$

Choose the closed loop transfer function to be a first order lag with desired bandwidth ω:

$$T(s) = \frac{\omega}{s + \omega} \quad \text{(Eq. 26)}$$

It should be noted that while a first order lag was chosen for the closed loop transfer function, because it yields the simplest control solution for the adaptive control, any stable T(s) would be suitable. Substituting equation 26 into equation 25 results in a compensator with the simple form of a lead/lag filter:

$$C(s) = \frac{\omega(s + k_3)}{k_1(s + k_2)} \quad \text{(Eq. 27)}$$

This compensator essentially cancels the non-zero poles and zeros of G(s), and provides the gain necessary to drive the remaining closed loop pole to ω. If the parameters of G(s) were fixed and known, T(s) could be perfectly realized. For a real lung circuit system, the parameters $k_1$, $k_2$ and $k_3$ change by such significant size that the system can never approach the desired T(s) with fixed compensator parameters. Thus a better approach would be to use real time estimates of the lung/circuit parameters to obtain $k_1$, $k_2$ and $k_3$ for real time adjustment of C(s):

$$k_1 = \frac{1}{\hat{C}_T} \quad \text{(Eq. 28)}$$

$$k_2 = \frac{1}{\hat{R}\hat{C}_L} \quad \text{(Eq. 29)}$$

$$k_3 = \frac{\hat{C}_L + \hat{C}_T}{\hat{R}\hat{C}_L\hat{C}_T} \quad \text{(Eq. 30)}$$

These parameters can be estimated using the method of recursive least squares. By using estimated parameters, an adaptive control structure is realized as illustrated in FIG. 3.

Here the pressure and flow measurements are used to estimate R, $C_T$ and $C_L$. $k_1$, $k_2$ and $k_3$ are then calculated for C(s) which tracks changes in G(s). The parameter estimates of R, $C_T$ and $C_L$ upon calculation should be limited to values within a reasonable range for these parameters before calculating $k_1$, $k_2$ and $k_3$. This will constrain the limits of the regulator and help prevent instability should the estimator experience an upset.

The lead/lag design of equation 27 is restructured into tandem high pass and low pass components to prevent control windup as:

$$\frac{Q(s)}{e(s)} = C(s) = \frac{\omega}{k_1}\left[\frac{s}{s + k_2} + \frac{k_3}{s + k_2}\right] \quad \text{(Eq. 31)}$$

The first term in the brackets is the high pass filter, the other the low pass filter. To obtain anti-windup operation when implemented as a discrete controller, the high pass function is first calculated. The output of the high pass function is then used to limit the integrator used in the low pass filter implementation such that the combined output never exceeds the saturation limits of the flow controller. The following paragraphs explain how the structure of equation 31 is implemented in discrete time.

The transfer function in equation 31 may be written as a discrete time approximation by assuming a sample time, T, and substituting the LaPlace operator, s, with equation 32. This expression uses the delay operator, $z^{-1}$ and accomplishes backward rectangular integration. The transformation maps left half complex poles and zeros completely within the unit circle in the z plane thus assuring stability.

$$s \to \frac{1-z^{-1}}{T} \quad \text{(Eq. 32)}$$

First tracking error, e(n) is calculated as:

$$e(n) = x(n) - Pc(n) \quad \text{(Eq. 33)}$$

Then the following set of equations implement the structure of equation 31:

$$y_{HP}(n) = \frac{1}{1+k_2T}\left[\frac{\omega}{k_1}(e(n)-e(n-1))+y_{HP}(n-1)\right] \quad \text{(Eq. 34)}$$

$$S(n) = \frac{k_3 T \omega}{k_1(1+k_2T)} e(n) + \frac{1}{1+k_2T} y_{LP}(n-1) \quad \text{(Eq. 35)}$$

$$y_{LP}(n) = \min\{\max\{(Q_{min}-y_{HP}(n)), S(n)\}, (Q_{max}-y_{HP}(n))\} \quad \text{(Eq. 36)}$$

Where $Q_{MIN}$ and $Q_{MAX}$ are the lower and upper limits of the flow control, respectively.

The output of C(s), Q(s) is then:

$$Q(n) = y_{HP}(n) + y_{LP}(n) \quad \text{(Eq. 37)}$$

This output is used to command the flow control. The flow control here is assumed to have dynamics which are far removed from the dynamics of G(s). Experiments show that to obtain even performance over the range of conditions from infant to adult, the flow control must provide at least a 15 msec. rise time over the entire flow range.

It is also possible to estimate $Q_L$, the flow into the patient lung, and $P_L$, the patient lung pressure, from the estimates of R, the airway resistance, $C_L$, the patient lung compliance, and $C_T$, the connecting circuit compliance, as is illustrated in equations 38 and 39 below.

$$Q_L(s) = \frac{\frac{1}{\hat{R}\hat{C}_T}}{s + \frac{\hat{C}_L + \hat{C}_T}{\hat{R}\hat{C}_L\hat{C}_T}} \cdot Q_V(s) \quad \text{(Eq. 38)}$$

$$\hat{P}_L(s) = \frac{\frac{1}{\hat{R}\hat{C}_L\hat{C}_T}}{s\left(s + \frac{\hat{C}_L + \hat{C}_T}{\hat{C}_L\hat{C}_T\hat{R}}\right)} \cdot Q_V(s) \quad \text{(Eq. 39)}$$

By discretizing equations 38 and 39, similar to the technique used in connection with equations 32 through 37 above, an anti-windup digital filter can be designed which provides real-time estimates of $Q_L$ and $P_L$, which are otherwise unmeasurable quantities.

While the invention has been described in the context of a controller for pressure based ventilation based upon estimates of parameters derived from measurements of patient ventilator airway variables, it will be appreciated that the controller of the invention can also be used to control the exhalation phase of a patient breath for either pressure based or volume based ventilation strategies. In such a case, the controller would act similarly to the pressure based intake system, but instead would use as targets the desired exhalation trajectories, while similarly deriving estimates of parameters based upon several variables in the exhalation airway. Similarly, a system using the invention could combine these sensed variables to control the ventilator to provide a desired inhalation and exhalation characteristic.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. In a method for determining real time estimates of patient airway resistance, patient lung compliance, and connecting tube circuit compliance, in a ventilator system providing gas at a desired pressure to a patient airway and lungs through a connecting tube circuit during pressure based ventilation, the method comprising the steps of:

measuring the flow of gas to the connecting tube circuit;

measuring the pressure of gas within the connecting tube circuit;

determining a real time estimate of patient airway resistance based upon the flow of gas to the connecting tube circuit and the pressure of gas within the connecting tube circuit;

determining a real time estimate of patient lung compliance based upon the flow of gas to the connecting tube circuit and the pressure of gas within the connecting tube circuit;

determining a real time estimate of the connecting tube circuit compliance based upon the flow of gas to the connecting tube circuit and the pressure of gas within the connecting tube circuit; and determining an estimate of the flow into the patient lungs from the estimates of the patient airway resistance, the patient lung compliance, and the connecting tube circuit compliance, by discretizing the following equation:

$$Q_L(s) = \frac{\frac{1}{\hat{R}\hat{C}_T}}{s + \frac{\hat{C}_L + \hat{C}_T}{\hat{R}\hat{C}_L\hat{C}_T}} \cdot Q_V(s)$$

where $Q_L$ is the flow into the patient lungs, R is the patient airway resistance, $C_L$ is the patient lung compliance, and $C_T$ is the connecting tube circuit compliance.

2. The method of claim 1, further comprising controlling the pressure of gas provided to the patient by the steps of:

determining a lung and connecting circuit transfer function for determining compensator parameters for compensating the pressure of gas delivered to the desired pressure based upon said real time estimates of patient airway resistance, patient lung compliance, and connecting tube circuit compliance;

comparing the actual pressure of gas within the connecting tube circuit and the desired pressure of gas, and generating an error signal representing the difference between said desired pressure and the actual pressure of gas within the connecting tube circuit; and compensating the pressure of gas provided to the patient airway to the desired pressure of gas to the patient airway based upon said desired pressure, and said compensator parameters, and said error signal representing the difference between said desired pressure and the actual pressure of gas within the connecting tube circuit.

3. In a method for determining real time estimates of patient airway resistance, patient lung compliance, and connecting tube circuit compliance, in a ventilator system providing gas at a desired pressure to a patient airway and lungs through a connecting tube circuit during pressure based ventilation, the method comprising the steps of:

measuring the flow of gas to the connecting tube circuit;

measuring the pressure of gas within the connecting tube circuit;

determining a real time estimate of patient airway resistance based upon the flow of gas to the connecting tube circuit and the pressure of gas within the connecting tube circuit;

determining a real time estimate of patient lung compliance based upon the flow of gas to the connecting tube circuit and the pressure of gas within the connecting tube circuit;

determining a real time estimate of the connecting tube circuit compliance based upon the flow of gas to the connecting tube circuit and the pressure of gas within the connecting tube circuit; and determining an estimate of the patient lung pressure from the estimates of the patient airway resistance, the patient lung compliance, and the connecting tube circuit compliance, by discretizing the following equation:

$$\hat{P}_L(s) = \frac{\frac{1}{\hat{R}\hat{C}_L\hat{C}_T}}{s\left(s + \frac{\hat{C}_L + \hat{C}_T}{\hat{C}_L\hat{C}_T\hat{R}}\right)} \cdot Q_V(s)$$

where $P_L$ is the patient lung pressure, R is the patient airway resistance, $C_L$ is the patient lung compliance, and $C_T$ is the connecting tube circuit compliance.

4. A method for controlling pressure of gas provided to a patient airway and lungs through a connecting tube circuit in a ventilation system providing pressure based ventilation, comprising the steps of:

providing pressurized gas to the patient airway through the connecting tube circuit;

determining a desired pressure of gas provided to the patient airway through the connecting tube circuit;

measuring the flow of gas to the connecting tube circuit;

measuring the pressure of gas within the connecting tube circuit;

determining a real time estimate of patient airway resistance based upon the flow of gas to the connecting tube circuit and the pressure of gas within the connecting tube circuit;

determining a real time estimate of patient lung compliance based upon the flow of gas to the connecting tube circuit and the pressure of gas within the connecting tube circuit;

determining a real time estimate of the connecting tube circuit compliance based upon the flow of gas to the connecting tube circuit and the pressure of gas within the connecting tube circuit;

determining an estimate of the flow into the patient lungs from the estimates of the patient airway resistance, the patient lung compliance, and the connecting tube circuit compliance, by discretizing the following equation:

$$Q_L(s) = \frac{\frac{1}{\hat{R}\hat{C}_T}}{s + \frac{\hat{C}_L + \hat{C}_T}{\hat{R}\hat{C}_L\hat{C}_T}} \cdot Q_V(s)$$

where $Q_L$ is the flow into the patient lungs, R is the patient airway resistance, $C_L$ is the patient lung compliance, and $C_T$ is the connecting tube circuit compliance;

determining a lung and connecting circuit transfer function for determining compensator parameters for compensating the pressure of gas delivered to the desired pressure based upon said real time estimates of patient airway resistance, patient lung compliance, and connecting tube circuit compliance;

comparing the pressure of gas within the connecting tube circuit and the desired pressure of gas, and generating an error signal representing the difference between said desired pressure and the pressure of gas within the connecting tube circuit; and compensating the pressure of gas provided to the patient airway to the desired pressure of gas to the patient airway based upon said desired pressure, and said compensator parameters, and said error signal representing the difference between said desired pressure and the pressure of gas within the connecting tube circuit.

5. In a method for controlling pressure of gas provided to a patient airway and lungs through a connecting tube circuit in a ventilation system providing pressure based ventilation, the method including the steps of providing pressurized gas to the patient airway through the connecting tube circuit; determining a desired pressure of gas provided to the patient airway through the connecting tube circuit; measuring the flow of gas to the connecting tube circuit; measuring the pressure of gas within the connecting tube circuit; comparing the pressure of gas within the connecting tube circuit and the desired pressure of gas, and generating an error signal representing the difference between said desired pressure and the pressure of gas within the connecting tube circuit; and compensating the pressure of gas provided to the patient airway to the desired pressure of gas to the patient airway based upon said desired pressure, and said error signal representing the difference between said desired pressure and the pressure of gas within the connecting tube circuit, the improvement comprising the steps of:

determining a real time estimate of patient airway resistance based upon the flow of gas to the connecting tube circuit and the pressure of gas within the connecting tube circuit;

determining a real time estimate of patient lung compliance based upon the flow of gas to the connecting tube circuit and the pressure of gas within the connecting tube circuit;

determining a real time estimate of the connecting tube circuit compliance based upon the flow of gas to the connecting tube circuit and the pressure of gas within the connecting tube circuit;

determining an estimate of the flow into the patient lungs from the estimates of the patient airway resistance, the patient lung compliance, and the connecting tube circuit compliance, by discretizing the following equation:

$$Q_L(s) = \frac{\frac{1}{\hat{R}\hat{C}_T}}{s + \frac{\hat{C}_L + \hat{C}_T}{\hat{R}\hat{C}_L\hat{C}_T}} \cdot Q_V(s)$$

where $Q_L$ is the flow into the patient lungs, R is the patient airway resistance, $C_L$ is the patient lung compliance, and $C_T$ is the connecting tube circuit compliance;

determining a lung and connecting circuit transfer function for determining compensator parameters for compensating the pressure of gas delivered to the desired pressure based upon said real time estimates of patient airway resistance, patient lung compliance, and connecting tube circuit compliance; and compensating the pressure of gas provided to the patient airway to the desired pressure of gas to the patient airway based upon said desired pressure, said compensator parameters, and said error signal representing the difference between said desired pressure and the pressure of gas within the connecting tube circuit.

6. In a method for determining real time estimates of patient airway resistance, patient lung compliance, and connecting tube circuit compliance, in a ventilator system providing gas at a desired pressure to a patient airway and lungs through a connecting tube circuit during volume based ventilation, the method to be used to control the exhalation phase of volume ventilation, the method comprising the steps of:

measuring the flow of gas in the exhalation circuit;

measuring the pressure of gas within the exhalation circuit;

determining a real time estimate of patient airway resistance based upon the flow of gas in the exhalation circuit and the pressure of gas within the exhalation circuit;

determining a real time estimate of patient lung compliance based upon the flow of gas in the exhalation circuit and the pressure of gas within the exhalation circuit;

determining a real time estimate of the exhalation circuit compliance based upon the flow of gas in the exhalation circuit and the pressure of gas within the exhalation circuit; and determining an estimate of the flow into the patient lungs from the estimates of the patient airway resistance, the patient lung compliance, and the connecting tube circuit compliance, by discretizing the following equation:

$$Q_L(s) = \frac{\frac{1}{\hat{R}\hat{C}_T}}{s + \frac{\hat{C}_L + \hat{C}_T}{\hat{R}\hat{C}_L\hat{C}_T}} \cdot Q_V(s)$$

where $Q_L$ is the flow into the patient lungs, R is the patient airway resistance, $C_L$ is the patient lung compliance, and $C_T$ is the connecting tube circuit compliance.

7. The method of claim 6, further comprising controlling the volume of gas provided to the patient by the steps of:

determining a lung and connecting circuit transfer function for determining compensator parameters for compensating the volume of gas delivered to the patient based upon said real time estimates of patient airway resistance, patient lung compliance, and connecting tube circuit compliance;

comparing the actual volume of gas within the connecting tube circuit and the desired pressure of gas, and generating an error signal representing the difference between said desired pressure and the actual pressure of gas within the connecting tube circuit; and compensating the volume of gas provided to the patient airway to the desired volume of gas to the patient airway based upon said desired pressure, and said resistance, patient lung compliance, and connecting tube circuit compliance; and compensating the pressure of gas provided to the patient airway to the desired pressure of gas to the patient airway based upon said desired pressure, said compensator parameters, and said error signal representing the difference between said desired pressure and the actual pressure of gas within the connecting tube circuit.

8. In a method for controlling pressure of gas provided to a patient airway and lungs through a connecting tube circuit in a ventilation system providing pressure based ventilation, the method including the steps of providing pressurized gas to the patient airway through the connecting tube circuit; determining a desired pressure of gas provided to the patient airway through the connecting tube circuit; measuring the flow of gas to the connecting tube circuit; measuring the pressure of gas within the connecting tube circuit; comparing the pressure of gas within the connecting tube circuit and the desired pressure of gas, and generating an error signal representing the difference between said desired pressure and the pressure of gas within the connecting tube circuit; and compensating the pressure of gas provided to the patient airway to the desired pressure of gas to the patient airway based upon said desired pressure, and said error signal representing the difference between said desired pressure and the pressure of gas within the connecting tube circuit, the improvement comprising the steps of:

determining a real time estimate of patient airway resistance based upon the flow of gas to the connecting tube circuit and the pressure of gas within the connecting tube circuit;

determining a real time estimate of patient lung compliance based upon the flow of gas to the connecting tube circuit and the pressure of gas within the connecting tube circuit;

determining a real time estimate of the connecting tube circuit compliance based upon the flow of gas to the connecting tube circuit and the pressure of gas within the connecting tube circuit;

determining an estimate of the patient lung pressure from the estimates of the patient airway resistance, the patient lung compliance, and the connecting tube circuit compliance, by discretizing the following equation:

$$\hat{P}_L(s) = \frac{\frac{1}{\hat{R}\hat{C}_L\hat{C}_T}}{s\left(s + \frac{\hat{C}_L + \hat{C}_T}{\hat{C}_L\hat{C}_T\hat{R}}\right)} \cdot Q_V(s)$$

where $P_L$ is the patient lung pressure, R is the patient airway resistance, $C_L$ is the patient lung compliance, and $C_T$ is the connecting tube circuit compliance;

determining a lung and connecting circuit transfer function for determining compensator parameters for compensating the pressure of gas delivered to the desired pressure based upon said real time estimates of patient airway resistance, patient, lung compliance, and connecting tube circuit compliance; and compensating the pressure of gas provided to the patient airway to the desired pressure of gas to the patient airway based upon said desired pressure, said compensator parameters, and said error signal representing the difference between said desired pressure and the pressure of gas within the connecting tube circuit.

9. In a method for determining real time estimates of patient airway resistance, patient lung compliance, and connecting tube circuit compliance, in a ventilator system providing gas at a desired pressure to a patient airway and lungs through a connecting tube circuit during volume based ventilation, the method to be used to control the exhalation phase of volume ventilation, the method comprising the steps of:

measuring the flow of gas in the exhalation circuit;

measuring the pressure of gas within the exhalation circuit;

determining a real time estimate of patient airway resistance based upon the flow of gas in the exhalation circuit and the pressure of gas within the exhalation circuit;

determining a real time estimate of patient lung compliance based upon the flow of gas in the exhalation circuit and the pressure of gas within the exhalation circuit;

determining a real time estimate of the exhalation circuit compliance based upon the flow of gas in the exhalation circuit and the pressure of gas within the exhalation circuit; and determining an estimate of the patient lung pressure from the estimates of the patient airway resistance, the patient lung compliance, and the connecting tube circuit compliance, by discretizing the following equation:

$$\hat{P}_L(s) = \frac{\frac{1}{\hat{R}\hat{C}_L\hat{C}_T}}{s\left(s + \frac{\hat{C}_L + \hat{C}_T}{\hat{C}_L\hat{C}_T\hat{R}}\right)} \cdot Q_V(s)$$

where $P_L$ is the patient lung pressure, R is the patient airway resistance, $C_L$ is the patient lung compliance, and $C_T$ is the connecting tube circuit compliance.

10. In a method for determining real time estimates of patient airway resistance, patient lung compliance, and connecting tube circuit compliance, in a ventilator system providing gas at a desired pressure to a patient airway and lungs through a connecting tube circuit during pressure based ventilation, the method comprising the steps of:

measuring the flow of gas to the connecting tube circuit;

measuring the pressure of gas within the connecting tube circuit;

determining a real time estimate of patient airway resistance based upon the flow of gas to the connecting tube circuit and the pressure of gas within the connecting tube circuit;

determining a real time estimate of patient lung compliance based upon the flow of gas to the connecting tube circuit and the pressure of gas within the connecting tube circuit;

determining a real time estimate of the connecting tube circuit compliance based upon the flow of gas to the connecting tube circuit and the pressure of gas within the connecting tube circuit; and determining an estimate of the patient lung pressure from the estimates of the patient airway resistance, the patient lung compliance, and the connecting tube circuit compliance, by discretizing the following equation:

$$\hat{P}_L(s) = \frac{\frac{1}{\hat{R}\hat{C}_L\hat{C}_T}}{s\left(s + \frac{\hat{C}_L + \hat{C}_T}{\hat{C}_L\hat{C}_T\hat{R}}\right)} \cdot Q_V(s)$$

where $P_L$ is the patient lung pressure, R is the patient airway resistance, $C_L$ is the patient lung compliance, and $C_T$ is the connecting tube circuit compliance; and controlling the pressure of gas provided to the patient by the steps of:

determining a lung and connecting circuit transfer function for determining compensator parameters for compensating the pressure of gas delivered to the desired pressure based upon said real time estimates of patient airway resistance, patient lung compliance, and connecting tube circuit compliance;

comparing the actual pressure of gas within the connecting tube circuit and the desired pressure of gas, and generating an error signal representing the difference between said desired pressure and the actual pressure of gas within the connecting tube circuit; and compensating the pressure of gas provided to the patient airway to the desired pressure of gas to the patient airway based upon said desired pressure, and said compensator parameters, and said error signal representing the difference between said desired pressure and the actual pressure of gas within the connecting tube circuit.

* * * * *